US005871740A

United States Patent [19]

Smith

[11] Patent Number: 5,871,740

[45] Date of Patent: Feb. 16, 1999

[54] METHODS OF USING POXVIRUS P35 AS A CHEMOKINE INHIBITOR AND COMPOSITIONS THEREFORE

[75] Inventor: Craig A. Smith, Seattle, Wash.

[73] Assignee: Immunex Corporation, Seattle, Wash.

[21] Appl. No.: 720,258

[22] Filed: Sep. 26, 1996

Related U.S. Application Data

[63] Continuation-in-part of Ser. No. 575,715, Dec. 20, 1995, abandoned, which is a continuation-in-part of Ser. No. 537,324, Sep. 29, 1995, abandoned.

[51] Int. Cl.[6] .................................................. A61K 39/275

[52] U.S. Cl. ....................... 424/186.1; 530/350; 530/403; 530/826; 435/69.3; 930/220

[58] Field of Search .................................... 435/7.1, 69.3; 514/2; 424/186.1; 530/350, 403, 826; 930/220

[56] References Cited

U.S. PATENT DOCUMENTS

| | | | |
|---|---|---|---|
| 5,157,110 | 10/1992 | Kotwal et al. | 530/350 |
| 5,453,364 | 9/1995 | Enzo Paoletti | 435/69.3 |

FOREIGN PATENT DOCUMENTS

| | | |
|---|---|---|
| WO 91/00911 | 1/1991 | WIPO . |
| WO 94/11504 | 5/1994 | WIPO . |
| WO 96/05856 | 2/1996 | WIPO . |

OTHER PUBLICATIONS

Ponath et al., "Cloning of the Human Eosinophil Chemoattractant, Eotaxin", *J. Clin. Invest.,* 97 (3):604–612, Feb. 1996.

Stellato et al., "Expression of the Chemokine RANTES by a Human Bronchial Epithelial Cell Line", *J. Immunol.,* pp. 410–418, 1995.

Dennis Michiel, "Chemokines: The Missing Link", *Bio/Technology,* 11 p. 739, Jun. 1993.

Geoffrey L. Smith, "Vaccinia virus glycoproteins and immune evasion", *J. General Virology,* 74:1725–1740, 1993.

Goebel et al., Appendix to "The Complete DNA Sequence of Vaccinia Virus", *Virology,* 179:517–563, 1990.

Massung et al., "Potential virulence determinants in terminal regions of variola smallpox virus genome", *Nature,* 366:748–751, Dec. 1993.

Oquendo et al., "The Platelet–derived Growth Factor–inducible KC Gene Encodes a Secretory Protein Related to Platelet α–Granule Proteins", *J. Biol. Chem.,* 264 (7):4133–4137, Mar. 5, 1989.

Karpus et al., "An Important Role for the Chemokine Macrophage Inflammatory Protein–1 α in the Pathogenesis of the T Cell–Mediated Autoimmune Disease, Experimental Autoimmune Encephalomyelitis", *J. Immunol.,* pp. 5503–5010, 1995.

Cook et al., "Requirements of MIP–1 α for an Inflammatory Response to Viral Infection", *Science,* 269:1583–1585, Sep. 15, 1995.

Baggiolini et al., "Interleukin–8 and Related Chemotactic Cytokines–CXC and CC Chemokines", *Advances in Immunology,* 55:97–179, 1994.

McCrae et al., "Specific Secretion of Polypeptides from Cells Infected with Vaccinia Virus", *J. Virol.,* 28:828–834, 1978.

Pickup et al., "Sequence of terminal regions of cowpox virus DNA: Arrangement of repeated and unique sequence elements", *Proc. Natl. Acad. Sci. USA,* 79:7112–7116, Dec. 1982.

Ray et al., "Viral Inhibition of Inflammation: Cowpox Virus Encodes an Inhibitor of the Interleukin–1β Converting Enzyme", *Cell,* 69:597–604, May 15, 1992.

Patel et al., "DNA sequence of the gene encoding a major secreted protein of vaccinia virus, strain Lister", *J. of General Virology,* 71:2013–2021, 1990.

Hu et al., "Cowpox Virus Contains Two Copies of an Early Gene Encoding a Soluble Secreted Form of the Type II TNF Receptor", *Virology,* 204:343–356, 1994.

Martinez–Pomares et al., "Mapping and Investigation of the Role in Pathogenesis of the Major Unique Secreted 35–kDa Protein of Rabbitpox Virus," *Virology,* 206:591–600, 1995.

Nandini V. Katre, "Immunogenicity of Recombinant IL–2 Modified by Covalent Attachment of Polyethylene Glycol," *J. Immunol.,* 144 (1):209–213, Jan. 1, 1990.

Shchelkunov et al., "Genes of variola and vaccinia viruses necessary to overcome the host protective mechanisms", *FEBS,* 319 (1 and 2):80–83, Mar. 1993.

Schall et al., "Selective attraction of monocytes and T lymphocytes of the memory phenotype by cytokine RANTES", *Nature,* 347:669–671, Oct. 18, 1990.

Marty et al., "Circulating interleukin–8 concentrations in patients with multiple organ failure of septic and nonseptic origin", *Critical Care Medicine,* 22 (4):673–679, 1994.

Cerretti et al., "The Murine Homologue of the Human Interleukin–8 Receptor Type B Maps near the Ity–Lsh–Bcg Disease Resistance Locus", *Genomics 18*:410–413, 1993.

Gao et al., "Cloning and Differential Tissue–specific Expression of Three Mouse β Chemokine Receptor–like Genes, Including the Gene for a Functional Macrophage Inflammatory Protein–1 α Receptor", *J. Biol. Chem.,* 270 (29):1794–17501, 1995.

Burgmann et al., "Serum Concentrations of MIP–1 α and Interleukin–8 in Patients Suffering from Acute *Plasmodium falciparum* Malaria", *Clinical Immunology and Immunopathology,* 76 (1):32–36, 1995.

(List continued on next page.)

*Primary Examiner*—Lorraine Spector
*Attorney, Agent, or Firm*—Janis C. Henry

[57] ABSTRACT

A protein designated p35 binds to a number of the chemotaxis-stimulating cytokines known as chemokines. p35 may be used to treat conditions that are mediated by chemokines, such as inflammation. p35 is a secreted protein that can be purified from the culture supernatant of cells infected with certain viruses, or produced using recombinant DNA techniques. Isolated DNA sequences encoding p35 are provided, along with expression vectors comprising the p35 DNA, and purified p35 protein.

29 Claims, 1 Drawing Sheet

OTHER PUBLICATIONS

Bump et al., "Inhibition of ICE Family Proteases by Baculovirus Antiapoptotic Protein p35", *Science,* 269:1885–1888, Sep. 29, 1995.

Kotwal et al., "Vaccinia virus encodes a secretory polypeptide structurally related to complement control proteins", *Nature,* 335:176–178, Sep. 8, 1988.

Tewari et al., "Yama/CPP32β, a Mammalian Homolog of CED–3, Is a CrmA–Inhibitable Protease That Cleaves the Death Substrate Poly(ADP–Ribose) Polymerase", *Cell,* 81:801–809, Jun. 2, 1995.

Enari et al., "Involvement of an ICE–like protease in Fas–mediated apoptosis", *Nature,* 375:78–83, May 4, 1995.

Nicholson et al., "Identification and inhibition of the ICE/CED–3 protease necessary for mammalian apoptosis", *Nature,* 376:37–43, Jul. 6, 1995.

Los et al., "Requirement of an ICE/CED–3 protease for Fas/APO–1–mediated apoptosis", *Nature 375*:81–83, 1995.

Patel, et al. J. Gen. Virol. vol. 71: pp. 2013–2021, 1990.

Remington's Pharmaceutical Sciences, 18th ed., (Gennaro, et al. eds.), p. 1398, Mack PublishingCompany, Eaton PA, 1990.

| Chemokine | cowpox p35/Fc |
|---|---|
| C-C Human: | |
| MCP-1/MCAF | + |
| MCP-2 | - |
| MCP-3 | + |
| Rantes | + |
| Eotaxin | + |
| C-C Mouse: | |
| MCP-1JE | + |
| MIP-1α | + |
| MIP-1β | + |
| C10 | + |
| Eotaxin | + |
| C-C Rat: | |
| MIP-1α | + |
| C-X-C Human: | |
| PF-4 | - |
| IP-10 | - |
| GROα | - |
| GROβ | - |
| GROγ | - |
| NAP-2 | - |
| IL-8 | - |
| ENA-78 | - |
| C-X-C Mouse: | |
| MIP-2 | - |
| KC | - |
| C-X-C Rat: | |
| GRO | - |

Figure 1

METHODS OF USING POXVIRUS P35 AS A CHEMOKINE INHIBITOR AND COMPOSITIONS THEREFORE

CROSS-REFERENCE TO RELATED APPLICATIONS

This application is a continuation-in-part of patent application U.S. Ser. No. 08/575,715, filed Dec. 20, 1995, now abandoned, which is a continuation-in-part of patent application U.S. Ser. No. 08/537,324, filed Sep. 29, 1995, now abandoned.

BACKGROUND OF THE INVENTION

Chemokines are a family of relatively small proteins that have been implicated as mediators of acute and chronic inflammation. Roles in other immunoregulatory processes have been reported for certain chemokines as well.

One branch of the chemokine family is characterized by the presence of an amino acid between the first two of four conserved cysteines, whereas a second branch lacks any amino acid between those two cysteine residues. The first branch has been designated the C-X-C branch or a subfamily, and the second is known as the C-C branch or β subfamily (Michiel, *Bio/Technology* 11:739, June 1993).

Chemokines have chemotactic properties, attracting certain cells of the immune system to sites of tissue injury and infection. Most of the α subfamily members attract and activate neutrophils, whereas β subfamily members attract monocytes. Certain β subfamily members additionally have been reported to recruit basophils, eosinophils or lymphocytes.

The roles chemokines play in various disorders is discussed in Baggiolini et al. (*Advances in Immunology* 55:97–179, 1994). Among the disorders believed to be mediated or exacerbated by one or more chemokines are inflammatory conditions of the lung (including inflammation associated with allergy or asthma) and skin (e.g., psoriasis). High levels of certain chemokines have been detected in the synovial fluid of inflamed joints in rheumatoid arthritis and osteoarthritis patients.

The chemokine macrophage inflammatory protein-1β (MIP-1β) suppresses hematopoietic stem cell proliferation, which has been suggested to contribute to anemia in malaria patients (Burgmann et al., *Clinical Immunology and Immunopathology* 76:32–36, 1995). The proinflammatory action of Interleukin-8 (IL-8) may play a role in deleterious host responses to sepsis (Marty et al., *Crit. Care Med.* 22:673–679, 1994). The possibility that monocyte chemoattractant protein-1 (MCP-1) and other C-C chemokines are involved in cardiovascular disease, through recruitment of monocytes into atherosclerotic areas, has been the subject of several studies (Baggiolini et al., supra, at page 146).

Inhibitors of chemokines would be useful in treating the disorders discussed above. A compound that inhibits more than one chemokine would be an especially desirable therapeutic agent.

SUMMARY OF THE INVENTION

The present invention provides a protein designated p35 that is capable of binding to chemokines. A method for treating a disorder mediated by a chemokine involves administering an effective amount of p35 to a mammal afflicted with such a disorder.

Isolated DNA sequences encoding p35 are also provided herein, along with expression vectors comprising the p35 DNA. Methods for producing recombinant p35 polypeptides involve culturing host cells containing the expression vectors under conditions appropriate for expression of p35, and recovering the expressed p35 from the cell culture. Certain embodiments of the invention are directed to p35 DNA derived from cowpox virus, the p35 protein encoded thereby, and uses thereof.

BRIEF DESCRIPTION OF THE DRAWINGS

FIG. 1 presents the results of the binding assay described in example 3. The assay tested the ability of a p35/Fc fusion protein to bind to a number of different chemokines. The+ symbol indicates that binding was detected.

DETAILED DESCRIPTION OF THE INVENTION

The ability of a protein designated p35 to bind multiple chemokines is disclosed herein. The present invention provides a method for inhibiting a biological activity of a chemokine by contacting the chemokine with a p35 polypeptide. A disorder mediated by a chemokine is treated by administering an effective amount of p35 to a mammal afflicted with such a disorder.

The present invention provides purified p35 polypeptides and pharmaceutical compositions containing such polypeptides. Isolated DNA sequences encoding p35 are provided herein, along with expression vectors comprising the p35 DNA. Methods for producing recombinant p35 polypeptides involve culturing host cells containing the expression vectors under conditions appropriate for expression of p35, and recovering the expressed p35 from the cell culture. Certain embodiments of the invention are directed to p35 DNA and polypeptides, and uses thereof.

A DNA and encoded amino acid sequence for cowpox p35 is presented in SEQ ID NO:1 and SEQ ID NO:2, respectively. Another p35 protein suitable for use in the present invention is encoded by an open reading frame in the genome of the Lister strain of vaccinia virus. DNA and amino acid sequences for this vaccinia virus p35 protein are presented in Patel et al. (*J. Gen. Virol.* 71:2013–2021, 1990; hereby incorporated by reference; note FIG. 4). Nucleotide and encoded amino acid sequences disclosed by Patel et al., supra, for p35 are also presented herein in SEQ ID NO:3 and SEQ ID NO:4, respectively. The cowpox p35 amino acid sequence in SEQ ID NO:2 is 86% identical to the vaccinia virus p35 amino acid sequence presented in SEQ ID NO:4.

Another suitable p35 protein is encoded by an open reading frame in the genome of the variola (smallpox) virus. A DNA sequence encoding this variola p35 protein is presented in SEQ ID NO:5. The amino acid sequence (shown in SEQ ID NO:6) is 82% identical to that of the cowpox p35 of SEQ ID NO:2, and 95% identical to that of the vaccinia p35 of SEQ ID NO:4.

The p35 proteins that may be employed in the methods disclosed herein include a genus of polypeptides that are substantially homologous to the p35 proteins of SEQ ID NOS:2, 4, or 6, and which exhibit the desired chemokine-binding property. The amino acid sequence of such p35 polypeptides preferably is at least 80%, most preferably at least 90%, identical to the sequence of SEQ ID NO:2 or SEQ ID NO:4 or SEQ ID NO:6. p35 polypeptides provided herein include, but are not limited to, fragments and variants of the native p35 proteins of SEQ ID NOS:2, 4, and 6. Such analogs are discussed in more detail below.

Homologs of certain viral proteins have been isolated from mammalian cell sources. Thus, the present invention encompasses homologs of the viral p35 proteins, wherein the homologs are derived from higher organisms, including mammalian cells. Cowpox p35 DNA may be radiolabeled and used as a probe in cross-species hybridization procedures, to detect p35 DNAs in the genomes of other virus strains, or in nucleic acids derived from cells of higher organisms.

The above-described p35 proteins are secreted proteins. A hydrophobic region at the N-terminus of the protein is believed to function as a signal peptide. The first 17 amino acids of vaccinia virus Lister strain p35 (numbered–17 through–1 in SEQ ID NO:4) have been predicted to constitute a signal sequence (Patel et al., supra), as have the first 16 amino acids of cowpox p35 and variola p35 (numbered–16 through–1 in SEQ ID NO:2 and SEQ ID NO:6, respectively). Thus, mature p35 proteins include those comprising amino acids 1 to 230 of SEQ ID NO:2, amino acids 1 to 241 of SEQ ID NO:4. and amino acids 1 to 236 of SEQ ID NO:6.

An alignment of amino acid sequences of several p35 proteins is presented in Martinez-Pomares et al. (Virology 206:591, 1995; see FIG. 3), along with a consensus sequence for orthopoxvirus p35 proteins. One of the sequences in the alignment corresponds to an open reading frame in the Copenhagan strain of vaccinia virus (VV-Copenhagan). This VV-Copenhagan sequence is Met-His-Val- followed by residues identical to amino acids 1 to 241 of SEQ ID NO:4. The VV-Copenhagan p35 protein thus lacks the signal peptide of the vaccinia virus Lister strain p35 of SEQ ID NO:4, but contains the residues corresponding to the mature protein of SEQ ID NO:4.

Regarding the foregoing discussion of signal peptides and mature p35 protein, the skilled artisan will recognize that the above-described boundaries of such regions of the protein are approximate. For example, although computer programs that predict the site of cleavage of a signal peptide are available, cleavage can occur at sites other than those predicted. Further, it is recognized that a protein preparation can comprise a mixture of protein molecules having different N-terminal amino acids, due to cleavage of the signal peptide at more than one site. In addition, post-translational processing can vary according to the particular expression system employed. Thus, the N- or C-terminal amino acid of a mature recombinant protein may vary according to the type of host cells in which the protein was expressed, for example.

Non-recombinant p35 may be purified from the culture supernatant of cells infected with p35-encoding viruses, as described below. Expression and purification of recombinant p35 is also discussed further below.

The ability of p35 to bind the following chemokines is reported in example 3 and FIG. 1:

MCP-1

MCP-3

RANTES

Eotaxin

MIP-1α

MIP-1β

C10

These chemokines are members of the C-C branch (β subfamily) of chemokines. The ability of p35 to bind to so many different chemokines is an advantageous property. When inflammation or another condition is mediated by more than one of these chemokines, the condition can be treated by administering p35 alone.

Additional chemokines that bind to p35 can be identified using conventional binding assay procedures. As one alternative, a p35 or p35/Fc protein can be immobilized on the chip of a biosensor unit. Binding of a chemokine to the immobilized p35 then can be tested as described in example 3.

A list of chemokines, the amino acid sequences thereof, and citations describing these proteins in more detail, are presented in Michiel, (*Bio/Technology* 11:739, June 1993), hereby incorporated by reference. Baggiolini et al. (*Advances in Immunology* 55:97–179, 1994), hereby incorporated by reference, describes a number of chemokines, including sources, activities, and structural features thereof. A number of chemokine proteins are commercially available, e.g., from Chemicon International, Inc., Temecula, Calif.; PeproTech, Inc., Rocky Hill, N.J.; and Genzyme Diagnostics, Cambridge, Mass.

Different chemokines exert a chemotactic effect on more than one cell type. Most C-X-C subfamily members attract and activate neutrophils, whereas C-C subfamily members attract monocytes but generally have no chemotactic effect on neutrophils. Certain C-C subfamily members additionally have been reported to recruit basophils, eosinophils or lymphocytes.

A number of chemokine receptors have been identified (reviewed in Baggiolini et al., supra, see pages 122–142). One notable structural feature of these receptors is that they contain seven transmembrane domains.

Chemokine-binding fragments of p35 polypeptides may be employed in the present invention. The ability of a p35 fragment to bind chemokines can be confirmed using a binding assay such as that described in example 3. p35 fragments may be prepared by any of a number of conventional techniques. A desired DNA sequence may be chemically synthesized, for example. DNA fragments also may be produced by restriction endonuclease digestion of a full length cloned DNA sequence, and isolated by electrophoresis on agarose gels. Linkers containing restriction endonuclease cleavage site(s) may be employed to insert the desired DNA fragment into an expression vector, or the fragment may be digested at cleavage sites naturally present therein. The well known polymerase chain reaction (PCR) procedure also may be employed to isolate a DNA sequence encoding a desired protein fragment. Oligonucleotides that define the termini of the desired fragment are employed as 5' and 3' primers in such a PCR procedure. As a further alternative, known mutagenesis techniques may be employed to insert a stop codon at a desired point, e.g., immediately downstream of the codon for the last amino acid of a desired fragment.

The present invention provides purified p35 polypeptides, both recombinant and non-recombinant. Variants and derivatives of native p35 proteins that retain the desired biological activity (e.g., the ability to bind at least one chemokine) are also within the scope of the present invention. p35 variants may be obtained by mutations of nucleotide sequences coding for native p35 polypeptides, for example. A p35 variant, as referred to herein, is a polypeptide substantially homologous to a native p35, but which has an amino acid sequence different from that of a native p35 because of one or more deletions, insertions or substitutions.

The variant amino acid sequence preferably is at least 80% identical, most preferably at least 90% identical to a native p35 amino acid sequence (such as the sequence of SEQ ID NO:2, 4, or 6. Variant DNA sequences provided herein are preferably at least 80% identical, most preferably at least 90% identical to a native p35 DNA sequence (such as the sequence of SEQ ID NO:1, 3, or 5). In one embodiment of the present invention, p35 DNA and amino acid sequences are at least 80% identical (preferably at least 90% identical) to the DNA sequence of SEQ ID NO:1 or the amino acid sequence presented in SEQ ID NO:2. In other embodiments of the invention, the amino acid sequence of the p35 protein is at least 95%, at least 96%, at least 97%, at least 98%, or at least 99% identical to the amino acid sequence presented in SEQ ID NO:2, SEQ ID NO:4, or SEQ ID NO:6.

The percent identity of DNA or amino acid sequences may be determined, for example, by comparing sequence information using a suitable computer program. One example is the GAP computer program, version 6.0, described by Devereux et al. (*Nucl. Acids Res.* 12:387, 1984) and available from the University of Wisconsin Genetics Computer Group (UWGCG). The GAP program utilizes the alignment method of Needleman and Wunsch (*J. Mol. Biol.* 48:443, 1970), as revised by Smith and Waterman (*Adv. Appi. Math* 2:482, 1981). The preferred default parameters for the GAP program include: (1) a unary comparison matrix (containing a value of 1 for identities and 0 for non-identities) for nucleotides, and the weighted comparison matrix of Gribskov and Burgess, *Nucl. Acids Res.* 14:6745, 1986, as described by Schwartz and Dayhoff, eds., *Atlas of Protein Sequence and Structure*, National Biomedical Research Foundation, pp. 353–358, 1979; (2) a penalty of 3.0 for each gap and an additional 0.10 penalty for each symbol in each gap; and (3) no penalty for end gaps.

Alterations of the native amino acid sequence may be accomplished by any of a number of known techniques. Mutations can be introduced at particular loci by synthesizing oligonucleotides containing a mutant sequence, flanked by restriction sites enabling ligation to fragments of the native sequence. Following ligation, the resulting reconstructed sequence encodes an analog having the desired amino acid insertion, substitution, or deletion.

Alternatively, oligonucleotide-directed site-specific mutagenesis procedures can be employed to provide an altered gene having particular codons altered according to the substitution, deletion, or insertion required. Methods of making the alterations set forth above are disclosed by Walder et al. (*Gene* 42:133, 1986); Bauer et al. (*Gene* 37:73, 1985); Craik (*BioTechniques*, January 1985, 12–19); Smith et al. (*Genetic Engineering: Principles and Methods*, Plenum Press, 1981); Kunkel (*Proc. Natl. Acad. Sci. USA* 82:488, 1985); Kunkel et al. (*Methods in Enzymol.* 154:367, 1987); and U.S. Pat. Nos. 4,518,584 and 4,737,462.

Variants may comprise conservatively substituted sequences, meaning that a given amino acid residue is replaced by a residue having similar physiochemical characteristics. Examples of conservative substitutions include substitution of one aliphatic residue for another, such as ile, Val, Leu, or Ala for one another, or substitutions of one polar residue for another, such as between Lys and Arg; Glu and Asp; or Gin and Asn. Other such conservative substitutions, for example, substitutions of entire regions having similar hydrophobicity characteristics, are well known. Conservatively substituted p35 polypeptides encompassed by the present invention are those that retain the ability to bind chemokines. Certain embodiments of p35 proteins contain from one to ten conservative amino acid substitutions. One embodiment of the present invention is directed to a p35 polypeptide comprising conservative substitution(s) in the amino acid sequence presented in SEQ ID NO:2, wherein the conservatively substituted polypeptide exhibits a biological activity that is essentially equivalent to that of the native protein of SEQ ID NO:2.

p35 also may be modified to create derivatives by forming covalent or aggregative conjugates with other chemical moieties, such as glycosyl groups, lipids, phosphate, acetyl groups and the like. Covalent derivatives of p35 may be prepared by linking the chemical moieties to functional groups on p35 amino acid side chains or at the N-terminus or C-terminus of a p35 polypeptide. Other derivatives of p35 within the scope of this invention include covalent or aggregative conjugates of p35 or its fragments with other proteins or polypeptides, such as by synthesis in recombinant culture as N-terminal or C-terminal fusions.

A p35 protein may be treated or derivatized to reduce the immunogenicity and antigenicity thereof. Such modification may be desirable if p35 is to be administered repeatedly to an individual, e.g., to treat a chronic condition. One approach involves attaching the polymer polyethylene glycol (PEG) to a p35 protein. Chemical modification with PEG has reduced the immunogenicity or antigenicity of a number of proteins (See Katre, N., *J. Immunol.* 144:209, 1990; and Delgado et al., *Critical Reviews in Therapeutic Drug Carrier Systems*, 9:249, 1992.) Modification with PEG has also been reported to increase the serum half-life and solubility of certain proteins. PEG may be covalently linked to lysine residues, to carbohydrate moieties on glycosylated proteins, or selectively to the N-terminus of proteins, for example. Modified p35 proteins can be tested in a suitable binding assay to confirm that the desired chemokine-binding property is retained.

Fragments of p35 may be less immunogenic than the corresponding full length proteins. The glycosylation pattern may affect the immunogenicity of a protein. As discussed above, glycosylation of recombinant proteins may be altered through the choice of host cells. p35 polypeptide fusions can comprise peptides added to facilitate purification and identification of p35. Such peptides include, for example, poly-His or the antigenic identification peptides described in U.S. Pat. No. 5,011,912 and in Hopp et al., *Bio/Technology* 6:1204, 1988. One such peptide is the FLAG® peptide, Asp-Tyr-Lys-Asp-Asp-Asp-Asp-Lys (DYKDDDDK) (SEQ ID NO:7), which is highly antigenic and provides an epitope reversibly bound by a specific monoclonal antibody enabling rapid assay and facile purification of expressed recombinant protein. This sequence is also specifically cleaved by bovine mucosal enterokinase at the residue immediately following the Asp-Lys pairing. Fusion proteins capped with this peptide may also be resistant to intracellular degradation in *E. coli*. A murine hybridoma designated 4E11 produces a monoclonal antibody that binds the peptide DYKDDDDK (SEQ ID NO:7) in the presence of certain divalent metal cations (as described in U.S. Pat. No. 5,011,912) and has been deposited with the American Type Culture Collection under accession no HB 9259.

The present invention further includes p35 polypeptides with or without associated native-pattern glycosylation. p35 expressed in yeast or mammalian expression systems (e.g., COS-7 cells) may be similar to or significantly different from a native p35 polypeptide in molecular weight and glycosylation pattern, depending upon the choice of expression system. Expression of p35 polypeptides in bacterial expression systems, such as *E. coli*, provides non-glycosylated molecules.

DNA constructs that encode various additions or substitutions of amino acid residues or sequences, or deletions of terminal or internal residues or sequences not needed for biological activity or binding can be prepared. For example, N-glycosylation sites in the p35 extracellular domain can be modified to preclude glycosylation, allowing expression of a more homogeneous, reduced carbohydrate analog in mammalian and yeast expression systems. N-glycosylation sites in eukaryotic polypeptides are characterized by an amino acid triplet Asn-X-Y, wherein X is any amino acid except Pro and Y is Ser or Thr. The p35 protein of SEQ ID NO:2 comprises one such triplet, at amino acids 156–158. The p35 protein of SEQ ID NO:4 contains an N-glycosylation site at amino acids 167–169; in the p35 protein of SEQ ID NO:6, amino acids 162–164 constitute an N-glycosylation site. Appropriate modifications to the nucleotide sequence encoding this triplet will result in substitutions, additions or deletions that prevent attachment of carbohydrate residues at the Asn side chain. Alteration of a single nucleotide, chosen so that Asn is replaced by a different amino acid, for example, is sufficient to inactivate an N-glycosylation site. Known procedures for inactivating N-glycosylation sites in proteins include those described in U.S. Pat. Nos. 5,071,972 and EP 276,846, hereby incorporated by reference.

In another example, codons for Cys residues that are not essential for biological activity can be altered to cause the Cys residues to be deleted or replaced with other amino acids. Formation of incorrect intramolecular disulfide bridges upon renaturation is thus prevented.

The present invention provides both non-naturally occurring and naturally occurring biologically active p35 variants. Examples of naturally occurring variants are proteins that result from proteolytic cleavage of the p35 protein, wherein the chemokine-binding property is retained. Variations attributable to proteolysis include, for example, differences in the N- or C-termini upon expression in different types of host cells, due to proteolytic removal of one or more terminal amino acids from the p35 protein (generally from 1–5 terminal amino acids). Naturally occurring variations in the DNA sequence may include silent mutations, for example, or deletions that do not result in a shift in the reading frame.

Due to the known degeneracy of the genetic code wherein more than one codon can encode the same amino acid, a DNA sequence may vary from that presented in SEQ ID NO:1, and still encode a p35 protein having the amino acid sequence of SEQ ID NO:2. Such variant DNA sequences may result from silent mutations (e.g., occurring during PCR amplification), and may be the product of deliberate mutagenesis of a native sequence.

Particular embodiments of p35-encoding DNAs are isolated DNAs comprising nucleotides 18 to 758 or 66 to 758 of SEQ ID NO:1. The DNA that comprises nucleotides 18 to 758 of SEQ ID NO:1 encodes a cowpox p35 protein that includes the native signal peptide, whereas a DNA having the sequence of nucleotides 66 to 758 encodes the mature form of the protein. The present invention provides isolated DNAs encoding a p35 protein comprising the amino acid sequence of residues–16 to 230 or 1 to 230 of SEQ ID NO:2. Also provided herein are isolated DNAs comprising nucleotides 1 to 777 or 52 to 777 of SEQ ID NO:3, as well as isolated DNAs comprising nucleotides 1 to 762 or 49 to 762 of SEQ ID NO:5.

Disclosed herein are isolated DNA sequences encoding biologically active p35, selected from: (a) the nucleotide sequence presented in SEQ ID NOS:1, 3, or 5; (b) DNA capable of hybridization to a nucleotide sequence of (a) under moderately or severely stringent conditions and which encodes a biologically active p35; and (c) DNA which is degenerate as a result of the genetic code to the nucleotide sequence defined in (a) or (b). The p35 proteins encoded by such DNA sequences are encompassed by the present invention.

Nucleic acid sequences disclosed herein include isolated DNA and RNA sequences that hybridize to native p35 nucleotide sequences under conditions of moderate or severe stringency, and which encode biologically active p35. For use in the therapeutic methods of the present invention, the desired biological activity of the encoded p35 is the ability to bind chemokines. Moderately stringent hybridization conditions refer to conditions described in, for example, Sambrook et al. *Molecular Cloning: A Laboratory Manual*, 2ed. Vol. 1, pp. 1.101–104, Cold Spring Harbor Laboratory Press, (1989). Conditions of moderate stringency, as defined by Sambrook et al., include use of a prewashing solution of 5×SSC, 0.5% SDS, 1.0 mM EDTA (pH 8.0) and hybridization at about 55° C., 5×SSC, overnight, followed by washing at 50°–55° C. in 2×SSC, 0.1% SDS. Conditions of severe stringency include higher temperatures of hybridization and washing. The skilled artisan will recognize that the temperature and wash solution salt concentration may be adjusted as necessary according to factors such as the length of the probe. Examples of p35-encoding DNA sequences include those that will hybridize to the nucleotide sequence of SEQ ID NOS:1, 3, or 5, under severely stringent conditions that include hybridization at 68° C. followed by washing in 0.1×SSC/0.1% SDS at 63°–68° C.

Examples of p35 proteins encoded by DNA that varies from the native DNA sequence of SEQ ID NOS:1, 3, or 5, wherein the variant DNA will hybridize to the native DNA sequence under moderately or severely stringent conditions, include, but are not limited to, p35 fragments and p35 proteins comprising inactivated N-glycosylation site(s), or conservative amino acid substitution(s), as described above. P35 proteins encoded by DNA derived from organisms other than cowpox virus, wherein the DNA will hybridize to the DNA of SEQ ID NO: 1, are also encompassed.

Variants possessing the requisite ability to bind chemokines may be identified by any suitable assay. A biosensor unit may be employed, as described in example 2. Alternatively, biological activity of a p35 variant may be determined by competition with a native p35 (e.g., the p35 of SEQ ID NO:2) for binding to a given chemokine (i.e. competitive binding assays). One type of a competitive binding assay employs a p35/Fc fusion protein bound to a solid phase through the interaction of the Fc moiety with Protein A or Protein G affixed to the solid phase. The ability of a p35 variant to inhibit binding of a labeled chemokine to the immobilized p35/Fc is analyzed by conventional techniques. Variants capable of binding at least one kind of chemokine find use, e.g., for binding that chemokine or treating a disease mediated by the chemokine.

p35 polypeptides may be employed as reagents in vitro assays. One example involves the use of p35 in screening assays to detect or isolate chemokines in a biological sample or cell culture.

Expression systems

The present invention provides recombinant expression vectors for expression of p35, and host cells transformed with the expression vectors. Any suitable expression system may be employed. The vectors include a p35 DNA sequence operably linked to suitable transcriptional or translational regulatory nucleotide sequences, such as those derived from a mammalian, microbial, viral, or insect gene. Examples of regulatory sequences include transcriptional promoters, operators, or enhancers, an mRNA ribosomal binding site, and appropriate sequences which control transcription and translation initiation and termination. Nucleotide sequences are operably linked when the regulatory sequence functionally relates to the p35 DNA sequence. Thus, a promoter nucleotide sequence is operably linked to a p35 DNA sequence if the promoter nucleotide sequence controls the transcription of the p35 DNA sequence. The ability to replicate in the desired host cells, usually conferred by an origin of replication, and a selection gene by which transformants are identified, may additionally be incorporated into the expression vector.

If desired, the native signal sequence may be replaced with a heterologous signal sequence. A signal peptide that promotes higher levels of secretion from a particular type of host cells than does the native signal peptide may be chosen, for example. A DNA sequence encoding the heterologous signal peptide (secretory leader) is fused in frame to the p35 sequence so that the p35 is initially translated as a fusion protein comprising the signal peptide. The signal peptide is cleaved from the p35 polypeptide upon secretion of p35 from the cell.

Suitable host cells for expression of p35 polypeptides include prokaryotes, yeast or higher eukaryotic cells. Appropriate cloning and expression vectors for use with bacterial, fungal, yeast, and mammalian cellular hosts are described, for example, in Pouwels et al. *Cloning Vectors: A Laboratory Manual*, Elsevier, New York, (1985). Cell-free translation systems could also be employed to produce p35 polypeptides using RNAs derived from DNA constructs disclosed herein.

Prokaryotes include gram negative or gram positive organisms, for example, *E. coli* or Bacilli. Suitable prokaryotic host cells for transformation include, for example, *E. coli, Bacillus subtilis, Salmonella typhimurium*, and various other species within the genera Pseudomonas, Streptomyces, and Staphylococcus. In a prokaryotic host cell, such as *E. coli*, an p35 polypeptide may include an N-terminal methionine residue to facilitate expression of the recombinant polypeptide in the prokaryotic host cell. The N-terminal Met may be cleaved from the expressed recombinant p35 polypeptide.

Expression vectors for use in prokaryotic host cells generally comprise one or more phenotypic selectable marker genes. A phenotypic selectable marker gene is, for example, a gene encoding a protein that confers antibiotic resistance or that supplies an autotrophic requirement. Examples of useful expression vectors for prokaryotic host cells include those derived from commercially available plasmids such as the cloning vector pBR322 (ATCC 37017). pBR322 contains genes for ampicillin and tetracycline resistance and thus provides simple means for identifying transformed cells. An appropriate promoter and a p35 DNA sequence are inserted into the pBR322 vector. Other commercially available vectors include, for example, pKK223-3 (Pharmacia Fine Chemicals, Uppsala, Sweden) and pGEM1 (Promega Biotec, Madison, Wis., USA).

Promoter sequences commonly used for recombinant prokaryotic host cell expression vectors include β-lactamase (penicillinase), lactose promoter system (Chang et al., *Nature* 275:615, 1978; and Goeddel et al., *Nature* 281:544, 1979), tryptophan (trp) promoter system (Goeddel et al., *Nucl. Acids Res.* 8:4057, 1980; and EP-A-36776) and tac promoter (Maniatis, *Molecular Cloning: A Laboratory Manual*, Cold Spring Harbor Laboratory, p. 412, 1982). A particularly useful prokaryotic host cell expression system employs a phage λ $P_L$ promoter and a cI857ts thermolabile repressor sequence. Plasmid vectors available from the American Type Culture Collection which incorporate derivatives of the λ $P_L$ promoter include plasmid pHUB2 (resident in *E. coli* strain JMB9 (ATCC 37092)) and pPLc28 (resident in *E. coli* RR1 (ATCC 53082)).

p35 alternatively may be expressed in yeast host cells, preferably from the Saccharomyces genus (e.g., *S. cerevisiae*). Other genera of yeast, such as Pichia or Kluyveromyces, may also be employed. Yeast vectors will often contain an origin of replication sequence from a 2μ yeast plasmid, an autonomously replicating sequence (ARS), a promoter region, sequences for polyadenylation, sequences for transcription termination, and a selectable marker gene. Suitable promoter sequences for yeast vectors include, among others, promoters for metallothionein, 3-phosphoglycerate kinase (Hitzeman et al., *J. Biol. Chem.* 255:2073, 1980) or other glycolytic enzymes (Hess et al., *J. Adv. Enzyme Reg.* 7:149, 1968; and Holland et al., *Biochem.* 17:4900, 1978), such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase. Other suitable vectors and promoters for use in yeast expression are further described in Hitzeman, EPA-73,657. Another alternative is the glucose-repressible ADH2 promoter described by Russell et al. (*J. Biol. Chem.* 258:2674, 1982) and Beier et al. (*Nature* 300:724, 1982). Shuttle vectors replicable in both yeast and *E. coli* may be constructed by inserting DNA sequences from pBR322 for selection and replication in *E. coli* ($Amp^r$ gene and origin of replication) into the above-described yeast vectors.

The yeast α-factor leader sequence may be employed to direct secretion of the p35 polypeptide. See, e.g., Kurjan et al., *Cell* 30:933, 1982; Bitter et al., *Proc. Natl. Acad. Sci. USA* 81:5330, 1984; U.S. Pat. No. 4,546,082; and EP 324,274. Other leader sequences suitable for facilitating secretion of recombinant polypeptides from yeast hosts are known to those skilled in the pertinent field.

Yeast transformation protocols are known to those of skill in the art. One such protocol is described by Hinnen et al., *Proc. Natl. Acad. Sci. USA* 75:1929, 1978. The Hinnen et al. protocol selects for $Trp^+$ transformants in a selective medium, wherein the selective medium consists of 0.67% yeast nitrogen base, 0.5% casamino acids, 2% glucose, 10 μg/ml adenine and 20 μg/ml uracil.

Yeast host cells transformed by vectors containing ADH2 promoter sequence may be grown for inducing expression in a "rich" medium. An example of a rich medium is one consisting of 1% yeast extract, 2% peptone, and 1% glucose supplemented with 80 μg/ml adenine and 80 μg/ml uracil. Derepression of the ADH2 promoter occurs when glucose is exhausted from the medium.

Mammalian or insect host cell culture systems could also be employed to express recombinant p35 polypeptides. Baculovirus systems for production of heterologous proteins in insect cells are reviewed by Luckow and Summers, *Bio/Technology* 6:47 (1988). Established cell lines of mammalian origin also may be employed. Examples of suitable mammalian host cell lines include the COS-7 line of monkey kidney cells (ATCC CRL 1651) (Gluzman et al., *Cell* 23:175, 1981), L cells, C127 cells, 3T3 cells (ATCC CCL 163), Chinese hamster ovary (CHO) cells, HeLa cells, and BHK (ATCC CRL 10) cell lines, and the CV-1/EBNA-1 cell line derived from the African green monkey kidney cell line CVI (ATCC CCL 70) as described by McMahan et al. (*EMBO J.* 10: 2821, 1991).

Transcriptional and translational control sequences for mammalian host cell expression vectors may be excised from viral genomes. Commonly used promoter sequences and enhancer sequences are derived from Polyoma virus, Adenovirus 2, Simian Virus 40 (SV40), and human cytomegalovirus. DNA sequences derived from the SV40 viral genome, for example, SV40 origin, early and late promoter, enhancer, splice, and polyadenylation sites may be used to provide other genetic elements for expression of a structural gene sequence in a mammalian host cell. Viral early and late promoters are particularly useful because both are easily obtained from a viral genome as a fragment which may also contain a viral origin of replication (Fiers et al., *Nature* 273:113, 1978). Smaller or larger SV40 fragments may also be used, provided the approximately 250 bp sequence extending from the Hind III site toward the Bgl I site located in the SV40 viral origin of replication site is included.

Expression vectors for use in mammalian host cells can be constructed as disclosed by Okayama and Berg (*Mol. Cell. Biol.* 3:280, 1983). A useful system for stable high level expression of mammalian cDNAs in C127 murine mammary epithelial cells is described by Cosman et al. (*Mol. Immunol.* 23:935, 1986). A high expression vector, PMLSV N1/N4, described by Cosman et al., *Nature* 312:768,1984 has been deposited as ATCC 39890. Additional suitable mammalian expression vectors are described in EP-A-0367566, and in PCT application WO 91/18982. In one embodiment, the vectors are derived from retroviruses.

A native p35 signal peptide is employed in the expression system described in example 1. Alternatively, DNA encoding a heterologous signal sequence (e.g., derived from a mammalian protein) may be added. Examples include the signal sequence for interleukin-7 (IL-7) described in U.S. Pat. No. 4,965,195; the signal sequence for interleukin-2 receptor described in Cosman et al., *Nature* 312:768 (1984); the interleukin-4 receptor signal peptide described in EP 367,566; the type I interleukin-1 receptor signal peptide described in U.S. Pat. No. 4,968,607; and the type II interleukin-1 receptor signal peptide described in EP 460, 846.

p35 Protein and Uses Thereof

The present invention provides purified p35 polypeptides, which may be produced by recombinant expression systems as described above or purified from naturally occurring cells. The desired degree of purity depends on the intended use of the protein. A relatively high degree of purity is desired when the protein is to be administered in vivo, for example.

Advantageously, p35 is purified such that no protein bands corresponding to other proteins are detectable by SDS-polyacrylamide gel electrophoresis (SDS-PAGE). It will be recognized by one skilled in the pertinent field that multiple bands corresponding to p35 protein may be detected by SDS-PAGE, due to differential glycosylation, variations in post-translational processing, and the like. A preparation of p35 protein is considered to be purified as long as no bands corresponding to different (non-p35) proteins are visualized. The p35 most preferably is purified to substantial homogeneity, as indicated by a single protein band upon analysis by SDS-PAGE. The protein band may be visualized by silver staining, Coomassie blue staining, or (if the protein is radiolabeled) by autoradiography.

One process for producing p35 comprises culturing a host cell transformed with an expression vector comprising a DNA sequence that encodes p35 under conditions such that p35 is expressed. The p35 protein is then recovered from the cell culture, using standard procedures. Advantageously, the expression vector encodes a signal peptide fused to the N-terminus of the p35, such that the p35 is secreted from the host cell and may be recovered from the culture medium.

For example, the culture medium first may be concentrated using a commercially available protein concentration filter, for example, an Amicon or Millipore Pellicon ultrafiltration unit. Following the concentration step, the concentrate can be applied to a purification matrix such as a gel filtration medium. Alternatively, an anion exchange resin can be employed, for example, a matrix or substrate having pendant diethylaminoethyl (DEAE) groups. The matrices can be acrylamide, agarose, dextran, cellulose or other types commonly employed in protein purification. Alternatively, a cation exchange step can be employed. Suitable cation exchangers include various insoluble matrices comprising sulfopropyl or carboxymethyl groups. Sulfopropyl groups are preferred. Finally, one or more reversed-phase high performance liquid chromatography (RP-HPLC) steps employing hydrophobic RP-HPLC media, (e.g., silica gel having pendant methyl or other aliphatic groups) can be employed to further purify p35. Some or all of the foregoing purification steps, in various combinations, can be employed to provide a substantially homogeneous recombinant protein.

It is also possible to utilize an immunoaffinity column containing an antibody that binds p35. Example 4 describes a procedure for employing a p35 protein to generate monoclonal antibodies reactive therewith.

Recombinant protein produced in bacterial culture is usually isolated by initial disruption of the host cells, centrifugation, extraction from cell pellets if an insoluble polypeptide, or from the supernatant fluid if a soluble polypeptide, followed by one or more concentration, salting-out, ion exchange, affinity purification or size exclusion chromatography steps. Finally, RP-HPLC can be employed for final purification steps. Microbial cells can be disrupted by any convenient method, including freeze-thaw cycling, sonication, mechanical disruption, or use of cell lysing agents.

Transformed yeast host cells are preferably employed to express p35 as a secreted polypeptide. This simplifies purification. Secreted recombinant polypeptide from a yeast host cell fermentation can be purified by methods analogous to those disclosed by Urdal et al. (*J. Chromatog.* 296:171, 1984). Urdal et al. describe two sequential, reversed-phase HPLC steps for purification of recombinant human IL-2 on a preparative HPLC column.

In one embodiment of the invention, non-recombinant p35 is purified by procedures analogous to those described in Patel et al., (*J. Gen. Virol.* 71:2013–2021, 1990) hereby incorporated by reference; see especially page 2014, column one. Briefly, suitable cells (e.g., rabbit kidney cells or CV1 cells) are infected with cowpox virus or vaccinia virus strain Lister, and incubated to allow secretion of p35 from the cells. The culture supernatant is collected, cells are removed (e.g., by centrifugation), and the supernatant is applied to an ion exchange column. Proteins are eluted from the column in a linear salt gradient, and the fraction containing the desired p35 protein is recovered.

Certain uses of p35 polypeptides flow from the chemokine-binding property thereof. One such use of p35 is as a reagent in protein purification procedures. p35 or p35/Fc fusion proteins may be attached to a solid support material by conventional techniques and used to purify chemokines by affinity chromatography. This use is illustrated in example 2.

p35 also finds use in inhibiting biological activity of chemokines. This use stems from the unexpected finding that p35 binds to chemokines, as reported in example 3. The ability of p35 to bind to several different chemokines is an especially advantageous property.

Chemokines have chemotactic properties, attracting certain cells of the immune system to sites of tissue injury and infection. Most of the α (CXC) subfamily members attract and activate neutrophils, whereas β (C-C) subfamily members generally attract monocytes. Certain β subfamily members additionally have been reported to recruit basophils, eosinophils or lymphocytes.

Chemokines are recognized as mediators of inflammation, both chronic and acute. Studies of the roles chemokines play in various disorders is reviewed in Baggiolini et al. (*Advances in Immunology* 55:97–179, 1994; hereby incorporated by reference; note especially pages 142–147). Among the disorders believed to be mediated, at least in part, by one or more chemokines are inflammatory conditions of the lung and skin, and inflammation associated with arthritis. Examples are lung inflammation associated with allergy or asthma. Interleukin-8 (IL-8), a C-X-C chemokine, is believed to play a role in causing the neutrophilic alveolitis in idiopathic pulmonary fibrosis (Baggiolini et al., supra, at pages 144–45). Monocyte chemoattractant protein-1 (MCP-1), a C-C chemokine, also has been implicated in fibrosis of the lung (Baggiolini et al., supra, at pages 144–45). Human MCP-1 is sometimes referred to as monocyte chemotactic and activating factor (MCAF), while an alternative designation for mouse MCP-1 is JE.

Overproduction of IL-8 has been linked to psoriasis, an inflammatory condition of the skin (see Baggiolini et al., supra, at page 145). High levels of certain chemokines have been detected in the synovial fluid of inflamed joints in rheumatoid arthritis and osteoarthritis patients (Baggiolini et al., supra, at pages 143–44).

The C-C chemokine macrophage inflammatory protein-1α (MP-1α) suppresses hematopoietic stem cell proliferation, which has been suggested to contribute to anemia in malaria patients (Burgmann et al., *Clinical Immunology and Immunopathology* 76:32–36, 1995). Chemokines are believed to play a role in certain conditions associated with viral infection. Studies in homozygous MIP-1α mutant (-/-) mice indicate that MIP-1α is a mediator of inflammation induced by viruses, examples of which are influenza virus and coxsackievirus B3 (CVB3) (Cook et al., *Science*, 269:1583, 1995). CVB3 infection causes myocarditis in young adults. The studies suggest that cardiac damage associated with myocarditis is not solely attributable to virus-mediated cytolysis, instead resulting (at least partially, perhaps largely) from the actions of recruited inflammatory cells (Cook et al., supra, at page 1585, column 1). The authors suggest that the absence of myocarditis in the MIP-1α (-/-) mice is likely due to an inability to recruit or retain mononuclear cells in the infected heart (Cook et al., supra, at page 1584, column 3). In influenza-infected MIP-1α (-/-) mutant mice, reduced lung inflammation was observed, although T-cell-dependent viral clearance was delayed (Cook et al., supra). The authors concluded that MIP-1 α contributes to influenza virus-induced pneumonitis.

MIP-1α is also believed to play a role in the pathogenesis of experimental autoimmune encephalomyelitis (EAE), a $CD4^+$ T cell-mediated inflammatory demyelinating disease of the central nervous system (Karpus et al., *J. Immunol.*, 155:5003, 1995). EAE is recognized as a model for the human disease multiple sclerosis.

The proinflammatory action of IL-8 may play a role in deleterious host responses to sepsis (Marty et al., *Crit. Care Med.* 22:673–679, 1994). The possibility that MCP-1 and other C-C chemokines are involved in cardiovascular disease, through recruitment of monocytes into atherosclerotic areas, has been the subject of several studies (Baggiolini et al., supra, at page 146).

Eotaxin, a member of the C-C subfamily, is a chemoattractant reported to be specific for eosinophils. Factors released by eosinophils contribute to hypersensitivity reactions. In the lungs of allergic asthmatic individuals, eosinophils accumulate and undergo degranulation. The resulting release of cytotoxic granule proteins aggravates lung tissue damage. The cloning of DNA encoding eotaxin, and certain functional properties of the protein, are described by Ponath et al. (*J. Clin. Invest.*, 97:604, 1996).

RANTES functions as a chemoattractant for eosinophils, monocytes, and $CD45RO^+$ memory T lymphocytes (Schall et al., *Nature*, 347:669, 1990; Stellato et al., *J. Immunol.*, 155:410, 1995). By contributing to cellular recruitment in the airways during inflammation, RANTES may play a role in the pathogenesis of conditions such as asthma, rhinitis, and polyposis (Stellato et al., supra).

The present invention provides a method of treating a disorder mediated by a chemokine, comprising administering an effective amount of a p35 polypeptide to a mammal afflicted with such a condition. Any of the forms of p35 polypeptides described herein may be employed, including, but not limited to, native p35 proteins and variants, derivatives, oligomers, and biologically active fragments thereof, as well as fusion proteins comprising p35. In particular embodiments of the invention, the mature form of the cowpox p35 of SEQ ID NO:2, the vaccinia virus p35 of SEQ ID NO:4, or the variola (smallpox) p35 of SEQ ID NO:6 is employed.

A disorder is said to be mediated by a chemokine if the chemokine causes or promotes, at least in part, or exacerbates the disorder. The chemokine may cause a condition indirectly, by the recruitment of cells to a particular site in vivo, or through the chemokine's effect on other biologically active molecules. In certain embodiments of the invention, the condition is mediated by one or more of the chemokines demonstrated to bind p35 in the assay of example 3.

In particular embodiments of the inventive method, p35 is administered to inhibit chemokine-mediated recruitment of cells, particularly cells involved in an inflammatory or autoimmune response. The p35 thus is employed to alleviate conditions resulting from the influx of such cells, e.g., at a site of inflammation or tissue injury. To illustrate, p35 may be administered to inhibit the influx of eosinophils into a site of lung tissue damage or inflammation. p35 proteins may be employed in treating those activated T cell-mediated or monocyte-mediated disorders in which chemokines play a role.

The p35 preferably is administered in the form of a pharmaceutical composition. p35 proteins can be formulated according to known methods that are used to prepare pharmaceutically useful compositions. Components that are commonly employed in pharmaceutical formulations are described in Remington's Pharmaceutical Sciences, 16th ed., 1980, Mack Publishing Company, for example.

Compositions of the present invention comprise an effective amount of a purified p35 polypeptide and a suitable (e.g., pharmaceutically acceptable) diluent, excipient, or carrier. Such carriers will be nontoxic to patients at the dosages and concentrations employed. The composition may additionally include a suitable emulsifier or preservative. Ordinarily, the preparation of such compositions may entail combining a p35 polypeptide with buffers, antioxidants such as ascorbic acid, low molecular weight (less than about 10 residues) peptides, proteins, amino acids, carbohydrates including glucose, sucrose, or dextrans, chelating agents such as EDTA, glutathione, or other stabilizers and excipients. Neutral buffered saline is one appropriate diluent. Pharmaceutical compositions suitable for inhalation are among the compositions contemplated herein.

p35 may be incorporated into polymeric compounds (such as polyacetic acid, polyglycolic acid, hydrogels, dextran, etc.) or incorporated into liposomes, microemulsions, micelles, unilamellar or multilamellar vesicles, erythrocyte ghosts or spheroblasts. Such compositions will influence the physical state, solubility, stability, rate of in vivo release, and rate of in vivo clearance of p35, and are thus chosen according to the intended application.

For therapeutic use, the compositions are administered in a manner and dosage appropriate to the indication and the patient. The amount administered will be effective in ameliorating the condition, by inhibiting the activity of a chemokine in vivo. As will be understood by one skilled in the pertinent field, a therapeutically effective dosage will vary according to such factors as the nature and severity of the condition, the location of affected tissue (e.g., the site of inflammation) within the body, and the age, condition and size of the patient. Administration may be by any suitable route, depending on the nature of the disorder, including but not limited to intravenous or local injection, inhalation, continuous infusion, local infusion during surgery, or sustained release from implants (such as gels, membranes, and the like).

Oligomeric Forms of p35

The present invention encompasses p35 polypeptides in the form of oligomers, such as dimers, trimers, or higher oligomers. Oligomers may be formed by disulfide bonds between cysteine residues on different p35 polypeptides, for example. In other embodiments, oligomers comprise from two to four p35 polypeptides joined by covalent or non-covalent interactions between peptide moieties fused to the p35 polypeptides. Such peptide moieties may be peptide linkers (spacers), or peptides that have the property of promoting oligomerization. Leucine zippers and certain polypeptides derived from antibodies are among the peptides that can promote oligomerization of p35 polypeptides attached thereto. DNA sequences encoding p35 oligomers, or fusion proteins that are components of such oligomers, are provided herein.

Preparation of fusion proteins comprising heterologous polypeptides fused to various portions of antibody-derived polypeptides (including the Fc domain) has been described, e.g., by Ashkenazi et al. (*PNAS USA* 88:10535, 1991), Byrn et al. (*Nature* 344:667, 1990), and Hollenbaugh and Aruffo ("Construction of Immunoglobulin Fusion Proteins", in *Current Protocols in Immunology*, Suppi. 4, pages 10.19.1 –10.19-11, 1992), hereby incorporated by reference. In one embodiment of the invention, a p35 dimer is created by fusing p35 to an Fc region polypeptide derived from an antibody, in a manner that does not interfere with binding of p35 to a chemokine of interest. A gene fusion encoding a p35/Fc fusion protein is inserted into an appropriate expression vector. The p35/Fc fusion proteins are allowed to assemble much like antibody molecules, whereupon interchain disulfide bonds form between Fc polypeptides, yielding divalent p35.

One suitable Fc polypeptide is the native Fc region polypeptide derived from a human IgG1, which is described in PCT application WO 93/10151, hereby incorporated by reference. Another useful Fc polypeptide is the Fc mutein described in U.S. Pat. No. 5,457,035. The amino acid sequence of the mutein is identical to that of the native Fc sequence presented in WO 93/10151, except that amino acid 19 has been changed from Leu to Ala, amino acid 20 has been changed from Leu to Glu, and amino acid 22 has been changed from Gly to Ala. This mutein Fc exhibits reduced affinity for immunoglobulin receptors.

In other embodiments, p35 may be substituted for the variable portion of an antibody heavy or light chain. If fusion proteins are made with both heavy and light chains of an antibody, it is possible to form a p35 oligomer with as many as four p35 polypeptides.

Alternatively, oligomeric p35 may comprise two or more p35 polypeptides joined through peptide linkers. Examples include those peptide linkers described in U.S. Pat. No. 5,073,627 (hereby incorporated by reference). Fusion proteins comprising multiple p35 polypeptides separated by peptide linkers may be produced using conventional recombinant DNA technology.

Another method for preparing p35 oligomers involves use of a leucine zipper. Leucine zipper domains are peptides that promote oligomerization of the proteins in which they are found. Leucine zippers were originally identified in several DNA-binding proteins (Landschulz et al., *Science* 240:1759, 1988), and have since been found in a variety of different proteins. Among the known leucine zippers are naturally occurring peptides and derivatives thereof that dimerize or trimerize. Examples of leucine zipper domains suitable for producing p35 oligomers are those described PCT application WO 94/10308, hereby incorporated by reference. Recombinant fusion proteins comprising a p35 polypeptide fused to a peptide that dimerizes or trimerizes in solution are expressed in suitable host cells, and the resulting soluble oligomeric p35 is recovered from the culture supernatant.

Antibodies p35 polypeptides may be employed as immunogens to generate antibodies, including polyclonal or monoclonal antibodies, by conventional procedures. See, for example, *Monoclonal Antibodies, Hybridomas: A New Dimension in Biological Analyses*, Kennet et al., eds., Plenum Press, New York (1980); and Antibodies: *A Laboratory Manual*, Harlow and Land, eds., Cold Spring Harbor Laboratory Press, Cold Spring Harbor, N.Y., (1988). One procedure for generating monoclonal antibodies specific for p35 is described in example 4.

Antigen-binding antibody fragments and derivatives may be prepared by conventional techniques. Examples of antibody fragments are Fab, F(ab'), and F(ab')2 fragments. One type of derivative is a chimeric antibody comprising a variable (or antigen-binding) region from a murine antibody, and the constant region of a human antibody. Procedures for producing chimeric and further engineered antibodies include those described in Riechmann et al. (*Nature* 332:323, 1988), Liu et al. (*PNAS USA* 84:3439, 1987), Larrick et al. (*Bio/Technology* 7:934, 1989), and Winter and Harris (*TIPS* 14:139, May, 1993).

Antibodies that are immunoreactive with p35 find use in purifying p35, e.g., by immunoaffinity chromatography. The antibodies also may be used to detect p35, e.g., in in vitro assays.

Nucleic Acid Fragments

The present invention further provides fragments of the p35 nucleotide sequences presented herein. Such fragments desirably comprise at least about 17 consecutive nucleotides, more preferably at least 30 consecutive nucleotides of the sequence presented in SEQ ID NOS: 1, 3, or 5. DNA and RNA complements of said fragments are provided herein, along with both single-stranded and double-stranded forms of p35 DNA.

Among the uses of such p35 nucleic acid fragments is use as a probe. Such probes may be employed in cross-species hybridization procedures to isolate p35 DNA from additional viral strains. The probes also find use in detecting the presence of p35 nucleic acids in in vitro assays and in such procedures as Northern and Southern blots. Cell types expressing p35 can be identified. Such procedures are well known, and the skilled artisan can choose a probe of suitable length, depending on the particular intended application. The probe may be labeled (e.g., with $^{32}$p) by conventional techniques.

p35 nucleic acid fragments also find use as primers in a polymerase chain reaction (PCR). 5' and 3' primers corresponding to the termini of a desired p35 DNA sequence are employed in isolating and amplifying the DNA, using conventional PCR techniques.

The following examples are provided to illustrate particular embodiments and not to limit the scope of the invention.

EXAMPLE 1

Preparation of 35/Fc Fusion Protein

This example describes preparation of a fusion protein comprising p35 fused to an Fc region polypeptide derived from an antibody. An expression vector encoding the p35/Fc fusion protein was constructed as follows.

DNA encoding the p35 protein of SEQ ID NO:2 (amino acids −16 to 230) was isolated by polymerase chain reaction (PCR). The oligonucleotide employed as the 5' primer in the PCR included nucleotides 1 to 24 of the DNA sequence of SEQ ID NO: 1, and contained an additional sequence that added a Not I restriction site upstream. The 3' primer included nucleotides complementary to nucleotides 733 to 755 of the DNA sequence of SEQ ID NO: 1 (which does not include the termination codon), a downstream sequence that encodes the first two amino acids of an Fc polypeptide, and a sequence that added a Bgl II restriction site downstream of the p35 and Fc sequences.

A recombinant vector containing cowpox DNA that included the p35 open reading frame was employed as the template in the PCR, which was conducted according to conventional procedures. The amplified DNA was digested with Not I and Bgl II, and the desired fragment was purified by electrophoresis on an agarose gel.

A DNA fragment encoding the Fc region of a human IgG1 antibody was isolated by digesting a vector containing cloned Fc-encoding DNA with Bgl II and Not I. Bgl II cleaves at a unique Bgl II site introduced near the 5' end of the Fc-encoding sequence, such that the Bgl II site encompasses the codons for amino acids three and four of the Fc polypeptide. Not I cleaves downstream of the Fc-encoding sequence. The nucleotide sequence of cDNA encoding the Fc polypeptide, along with the encoded amino acid sequence, are presented in PCT application publication no. WO93/10151, hereby incorporated by reference.

In a three-way ligation, the above-described p35-encoding DNA and Fc-encoding DNA were inserted into an expression vector that had been digested with Not I and treated with a phosphatase to minimize recircularization of any vector DNA without an insert. The vector, pDC406 (described in McMahan et al., *EMBO J.* 10:2821, 1991), is a mammalian expression vector that is also capable of replication in *E. coli.*

*E. coli* cells were transfected with the ligation mixture, and the desired recombinant vector was isolated. The vector encodes amino acids−16 to 230 of the p35 sequence of SEQ ID NO:2, fused to the N-terminus of the Fc polypeptide. The encoded Fc polypeptide extends from the N-terminal hinge region to the native C-terminus, i.e., is an essentially full-length antibody Fc region.

CV-1/EBNA-1 cells (ATCC CRL 10478) were transfected with the recombinant vector by conventional procedures. The CVI-EBNA-1 cell line was derived from the African Green Monkey kidney cell line CV-1 (ATCC CCL 70), as described by McMahan et al. (*EMBO J.* 10:2821, 1991). The transfected cells were cultured to allow transient expression of the p35/Fc fusion protein, which was secreted into the culture medium. The secreted protein contains the mature form of p35, fused to the Fc polypeptide. The p35/Fc proteins are believed to form dimers, wherein two such fusion proteins are joined by disulfide bonds that form between the Fc moieties thereof. The p35/Fc protein was recovered from the culture medium by affinity chromatography on a Protein A-bearing chromatography column.

EXAMPLE 2

Identification of a Factor that binds p35

Several dozen cell lines were tested for the ability to bind the p35/Fc fusion protein described in example 1. A variety of cell types, both normal and tumor cells, were tested, including but not limited to B-cells and T-cells (activated and non-activated), macrophages, epithelial cells, and fibroblasts. None of the cell lines bound p35/Fc.

Supernatants from a representative panel of cell lines were tested to determine whether any secreted proteins would bind p35/Fc. The p35/Fc protein was immobilized on the chip of a biosensor unit, as follows. Goat anti-human IgG directed against the Fc region (Jackson Immunoresearch Laboratories, Inc., West Grove, Pa.) was chemically bound to the chip of a BIAcore Processing Unit (Pharmacia Biosensor) by standard techniques. The p35/Fc protein was then bound to the immobilized goat anti-human IgG via interaction of the antibody with the Fc moiety of the fusion protein.

Supernatants from cultures of the cell lines then were allowed to flow across the chip. The culture medium from one cell line, a murine thymic epithelial cell line designated TE71, was found to contain a protein that bound to p35/Fc. The binding was indicated by a significant resonance shift on the Biosensor. TE71 cells then were metabolically labeled with $^{35}$S so that the proteins produced by the cells could be visualized. p35/Fc was shown to immunoprecipitate a diffuse 25 kD protein from the TE71 culture supernatant. The 25 kD protein was purified by affinity chromatography, using a column containing p35/Fc. Determination of the amino acid sequence revealed that the 25 kD protein was a chemokine known as JE or murine monocyte chemoattractant protein-1 (MCP-1) (Rollins, PNAS 85:3738, 1988).

EXAMPLE 3

Chemokines that bind P35

Since JE bound p35/Fc, additional chemokines were tested for the ability to bind cowpox p35/Fc immobilized on a biosensor. The results are shown in FIG. 1, in which+ indicates binding.

EXAMPLE 4

Monoclonal Antibodies to p35

This example illustrates the preparation of monoclonal antibodies directed against p35. Purified p35 (or an immunogenic fragment thereof) can be used to generate monoclonal antibodies using conventional techniques such as those described in U.S. Pat. No. 4,411,993. Briefly, mice are immunized with p35 as an immunogen emulsified in complete Freund's adjuvant, and injected in amounts ranging from 10–100 μg subcutaneously or intraperitoneally. Ten to twelve days later, the immunized animals are boosted with additional p35 emulsified in incomplete Freund's adjuvant. Mice are periodically boosted thereafter on a weekly to bi-weekly immunization schedule. Serum samples are periodically taken by retro-orbital bleeding or tail-tip excision for testing by dot blot assay or ELISA (Enzyme-Linked Immunosorbent Assay), for p35 antibodies.

Following detection of an appropriate antibody titer, positive animals are provided one last intravenous injection of p35 in saline. Three to four days later, the animals are sacrificed, spleen cells harvested, and spleen cells are fused to a murine myeloma cell line, e.g., NS 1 or preferably P3×63Ag8.653 (ATCC CRL 1580). Fusions generate hybridoma cells, which are plated in multiple microtiter plates in a HAT (hypoxanthine, aminopterin and thymidine) selective medium to inhibit proliferation of non-fused cells, myeloma hybrids, and spleen cell hybrids.

The hybridoma cells are screened by ELISA for reactivity against purified p35 by adaptations of the techniques disclosed in Engvall et al. (*Immunochem.* 8:871, 1971) and in U.S. Pat. No. 4,703,004. A preferred screening technique is the antibody capture technique described in Beckmann et al. (*J. Immunol.* 144:4212, 1990) Positive hybridoma cells can be injected intraperitoneally into syngeneic BALB/c mice to produce ascites containing high concentrations of anti-p35 monoclonal antibodies. Alternatively, hybridoma cells can be grown in vitro in flasks or roller bottles by various techniques. Monoclonal antibodies produced in mouse ascites can be purified by ammonium sulfate precipitation, followed by gel exclusion chromatography. Alternatively, affinity chromatography based upon binding of antibody to protein A or protein G can also be used, as can affinity chromatography based upon binding to p35.

What is claimed is:

1. A method of binding an isolated chemokine, the method comprising causing an isolated poxvirus encoded p35 polypeptide, capable of binding the chemokine, to contact the isolated chemokine.

2. A method of treating a condition mediated by a chemokine, comprising administering an effective amount of an isolated poxvirus encoded p35 polypeptide, capable of binding the chemokine, to a mammal afflicted with said condition.

3. A method of claim 1 or 2, wherein said p35 polypeptide comprises an amino acid sequence that is at least 80% identical to a sequence selected from the group consisting of:

a) residues 1 to 230 of SEQ ID NO:2;

b) residues 1 to 241 of SEQ ID NO:4; and c) residues 1 to 237 of SEQ ID NO:6, wherein said p35 polypeptide binds a chemokine wherein percent identity is calculated using the GAP program with a unary comparison matrix, a 3.0 gap penalty, an additional 0.10 penalty for each symbol in each gap, and no penalty for end gaps.

4. A method of claim 3, wherein said p35 polypeptide comprises an amino acid sequence that is at least 90% identical to the sequence of residues 1 to 230 of SEQ ID NO:2, wherein percent identity is calculated as set forth in claim 3.

5. A method of claim 4, wherein said p35 polypeptide comprises the sequence of residues 1 to 230 of SEQ ID NO:2.

6. A method of claim 3, wherein said p35 polypeptide comprises an amino acid sequence that is at least 90% identical to the sequence of residues 1 to 241 of SEQ ID NO:4, wherein percent identity is calculated as set forth in claim 3.

7. A method of claim 6, wherein said p35 polypeptide comprises the sequence of residues 1 to 241 of SEQ ID NO:4.

8. A method of claim 3, wherein said p35 polypeptide comprises an amino acid sequence that is at least 90% identical to the sequence of residues 1 to 237 of SEQ ID NO:6, wherein percent identity is calculated as set forth in claim 3.

9. A method of claim 8, wherein said p35 polypeptide comprises the sequence of residues 1 to 237 of SEQ ID NO:6.

10. A method of claim 1 or 2, wherein said p35 polypeptide is a fragment of a p35 protein selected from the group consisting of the p35 protein of SEQ ID NO:2, the p35 protein of SEQ ID NO:4, and the p35 protein of SEQ ID NO:6, wherein said fragment is capable of binding a chemokine.

11. A method of claim 1 or 2, wherein said p35 polypeptide is encoded by a DNA selected from the group consisting of:

a) a DNA comprising nucleotides 18 to 758 of SEQ ID NO:1;

b) a DNA comprising nucleotides 1 to 777 of SEQ ID NO:3;

c) a DNA comprising nucleotides 1 to 762 of SEQ ID NO:5;

d) a DNA that is degenerate as a result of the genetic code to a DNA of (a), (b), or (c); and e) a DNA capable of hybridizing under severely stringent conditions to a DNA of (a), (b), or (c);

wherein said p35 polypeptide is capable of binding a chemokine.

12. A method of claim 1 or 2, wherein said chemokine is a member of the β subfamily of chemokines.

13. A method of claim 12, wherein said chemokine is selected from the group consisting of monocyte chemotactic protein-1, monocyte chemotactic protein-3, Rantes, Eotaxin, macrophage inflammatory protein-1α, and macrophage inflammatory protein -1β.

14. A method of claim 2, wherein said condition is inflammation.

15. A method of claim 14, wherein said condition is inflammation of the lungs.

16. A method of claim 2, wherein said mammal is a human.

17. A method of claim 2 wherein said condition is influenza.

18. A method of claim 1 or 2, wherein said p35 polypeptide is in the form of an oligomer comprising from two to four p35 polypeptides, wherein each of the p35 polypeptides comprises an amino acid sequence that is at least 80% identical to a sequence selected from the group consisting of:

a) residues 1 to 230 of SEQ ID NO:2;

b) residues 1 to 241 of SEQ ID NO:4; and c) residues 1 to 237 of SEQ ID NO:6, wherein percent identity is calculated using the GAP program with a unary comparison matrix, a 3.0 gap penalty, an additional 0.10 penalty for each symbol in each gap, and no penalty for end gaps.

19. A method of claim 18, wherein each of the p35 polypeptides comprises an amino acid sequence selected from the group consisting of:

a) residues 1 to 230 of SEQ ID NO:2;

b) residues 1 to 241 of SEQ ID NO:4; and c) residues 1 to 237 of SEQ ID NO:6.

20. A method of claim 18, wherein said oligomer is a dimer comprising two p35/Fc fusion proteins.

21. A method of treating inflammation, comprising administering an effective amount of a p35 polypeptide to a mammal afflicted with an inflammatory condition, wherein said p35 polypeptide is selected from the group consisting of:

a) a polypeptide comprising residues 1 to 230 of SEQ ID NO:2;

b) a polypeptide comprising residues 1 to 241 of SEQ ID NO:4; and c) a polypeptide comprising residues 1 to 237 of SEQ ID NO:6.

22. A method of claim 21, wherein said mammal is a human.

23. A pharmaceutical composition for treatment of a chemokine mediated condition comprising an isolated p35 polypeptide and a pharmaceutically acceptable diluent, excipient, or carrier, wherein said isolated p35 polypeptide comprises an amino acid sequence that is at least 80% identical to a sequence selected from the group consisting of:

a) residues 1 to 230 of SEQ ID NO:2;

b) residues 1 to 241 of SEQ ID NO:4; and c) residues 1 to 237 of SEQ ID NO:6, wherein percent identity is calculated using the GAP program with a unary comparison matrix, a 3.0 gap penalty, an additional 0.10 penalty for each symbol in each gap, and no penalty for end gaps.

24. A composition of claim 23, wherein said isolated p35 polypeptide comprises an amino acid sequence selected from the group consisting of:

a) residues 1 to 230 of SEQ ID NO:2;

b) residues 1 to 241 of SEQ ID NO:4; and c) residues 1 to 237 of SEQ ID NO:6.

25. A purified oligomer comprising from two to four p35 polypeptides, wherein the oligomer is capable of binding a chemokine and each of the p35 polypeptides comprises an amino acid sequence that is at least 80% identical to a sequence selected from the group consisting of:

a) residues 1 to 230 of SEQ ID NO:2;

b) residues 1 to 241 of SEQ ID NO:4; and c) residues 1 to 237 of SEQ ID NO:6, wherein percent identity is calculated using the GAP program with a unary comparison matrix, a 3.0 gap penalty, an additional 0.10 penalty for each symbol in each gap, and no penalty for end gaps.

26. An oligomer of claim 25, wherein each of the p35 polypeptides comprises an amino acid sequence selected from the group consisting of:

a) residues 1 to 230 of SEQ ID NO:2;

b) residues 1 to 241 of SEQ ID NO:4; and c) residues 1 to 237 of SEQ ID NO:6.

27. An oligomer of claim 26, wherein said oligomer is a dimer comprising two p35/Fc fusion proteins.

28. A pharmaceutical composition for treatment of a chemokine mediated condition comprising an oligomer of claim 25 and a pharmaceutically acceptable diluent, excipient, or carrier.

29. A pharmaceutical composition for treatment of a chemokine mediated condition comprising an isolated poxvirus encoded p35 polypeptide and a pharmaceutically acceptable diluent, excipient or carrier.

* * * * *

SEQUENCE LISTING ( 1 ) GENERAL INFORMATION:

( i i i ) NUMBER OF SEQUENCES: 7

( 2 ) INFORMATION FOR SEQ ID NO:1:

( i ) SEQUENCE CHARACTERISTICS:
( A ) LENGTH: 758 base pairs
( B ) TYPE: nucleic acid
( C ) STRANDEDNESS: single
( D ) TOPOLOGY: linear ( i i ) MOLECULE TYPE: cDNA ( i i i ) HYPOTHETICAL: NO ( i v ) ANTI-SENSE: NO ( v i i ) IMMEDIATE SOURCE:
( B ) CLONE: Cowpox p35

( i x ) FEATURE:
( A ) NAME/KEY: CDS
( B ) LOCATION: 18..758

( i x ) FEATURE:
( A ) NAME/KEY: mat_peptide
( B ) LOCATION: 66..755

( i x ) FEATURE:
( A ) NAME/KEY: sig_peptide
( B ) LOCATION: 18..65

( x i ) SEQUENCE DESCRIPTION: SEQ ID NO:1:

```
CATCTAGAAC AGCAATC ATG AAA CAA ATC GTC CTG GCA TGC ATA TGC CTG         50
                   Met Lys Gln Ile Val Leu Ala Cys Ile Cys Leu
                   -16 -15                 -10

GCG GCA GTT GCT ATC CCT ACC AGT CTT CAG CAA TCA TTC TCA TCC TCA        98
Ala Ala Val Ala Ile Pro Thr Ser Leu Gln Gln Ser Phe Ser Ser Ser
 -5                  1                   5                  10

TCC TCG TGT ACG GAA GAA GAA AAC AAA CAT CAT ATG GGA ATC GAT GTT       146
Ser Ser Cys Thr Glu Glu Glu Asn Lys His His Met Gly Ile Asp Val
            15                  20                  25

ATT ATC AAA GTC ACC AAG CAA GAC CAA ACA CCG ACC AAT GAT AAG ATT       194
Ile Ile Lys Val Thr Lys Gln Asp Gln Thr Pro Thr Asn Asp Lys Ile
        30                  35                  40
```

-continued

TGT CAA TCA GTA ACC GAA GTT ACA GAG TCT GAA GAC GAG TCA GAA GAA 242
Cys Gln Ser Val Thr Glu Val Thr Glu Ser Glu Asp Glu Ser Glu Glu
45 50 55

GTC GTA AAG GGA GAT CCC ACC ACT TAT TAC ACT GTC GTC GGT GGA GGT 290
Val Val Lys Gly Asp Pro Thr Thr Tyr Tyr Thr Val Val Gly Gly Gly
60 65 70 75

CTT ACG ATG GAC TTT GGA TTC ACC AAA TGC CCA AAG ATT TCA TCC ATC 338
Leu Thr Met Asp Phe Gly Phe Thr Lys Cys Pro Lys Ile Ser Ser Ile
80 85 90

TCT GAA TAC TCT GAC GGA AAC ACT GTG AAT GCT AGA TTG TCT AGC GTG 386
Ser Glu Tyr Ser Asp Gly Asn Thr Val Asn Ala Arg Leu Ser Ser Val
95 100 105

TCC CCA GGA CAA GGT AAG GAC TCT CCC GCT ATC ACT CGT GAA GAA GCT 434
Ser Pro Gly Gln Gly Lys Asp Ser Pro Ala Ile Thr Arg Glu Glu Ala
110 115 120

CTG TCT ATG ATC AAA GAC TGT GAA ATG TCT ATC AAC ATC AAA TGT AGC 482
Leu Ser Met Ile Lys Asp Cys Glu Met Ser Ile Asn Ile Lys Cys Ser
125 130 135

GAA GAA GAG AAA GAC AGC AAC ATC AAG ACC CAT CCA GTA CTC GGG TCT 530
Glu Glu Glu Lys Asp Ser Asn Ile Lys Thr His Pro Val Leu Gly Ser
140 145 150 155

AAC ATC TCC CAT AAG AAA GTG AGT TAC GAA GAT ATC ATC GGA TCA ACG 578
Asn Ile Ser His Lys Lys Val Ser Tyr Glu Asp Ile Ile Gly Ser Thr
160 165 170

ATC GTC GAT ACG AAA TGC GTC AAG AAT CTA GAG ATT AGC GTT CGT ATA 626
Ile Val Asp Thr Lys Cys Val Lys Asn Leu Glu Ile Ser Val Arg Ile
175 180 185

GGA GAC ATG TGC AAG GAA TCA TCT GAA CTT GAG GTC AAG GAT GGA TTC 674
Gly Asp Met Cys Lys Glu Ser Ser Glu Leu Glu Val Lys Asp Gly Phe
190 195 200

AAG TAT GTC GAC GGA TCG GCA TCG GAA GAT GCA GCC GAT GAT ACT TCA 722
Lys Tyr Val Asp Gly Ser Ala Ser Glu Asp Ala Ala Asp Asp Thr Ser
205 210 215

CTC ATC AAT TCA GCA AAA CTT ATA GCG TGT GTC TGA 758
Leu Ile Asn Ser Ala Lys Leu Ile Ala Cys Val *
220 225 230

( 2 ) INFORMATION FOR SEQ ID NO:2:

( i ) SEQUENCE CHARACTERISTICS:
( A ) LENGTH: 246 amino acids
( B ) TYPE: amino acid
( D ) TOPOLOGY: linear ( i i ) MOLECULE TYPE: protein ( x i ) SEQUENCE DESCRIPTION: SEQ ID NO:2:

Met Lys Gln Ile Val Leu Ala Cys Ile Cys Leu Ala Ala Val Ala Ile
-16 -15 -10 -5

Pro Thr Ser Leu Gln Gln Ser Phe Ser Ser Ser Ser Ser Cys Thr Glu
1 5 10 15

Glu Glu Asn Lys His His Met Gly Ile Asp Val Ile Ile Lys Val Thr
20 25 30

Lys Gln Asp Gln Thr Pro Thr Asn Asp Lys Ile Cys Gln Ser Val Thr
35 40 45

Glu Val Thr Glu Ser Glu Asp Glu Ser Glu Glu Val Val Lys Gly Asp
50 55 60

Pro Thr Thr Tyr Tyr Thr Val Val Gly Gly Gly Leu Thr Met Asp Phe
65 70 75 80

Gly Phe Thr Lys Cys Pro Lys Ile Ser Ser Ile Ser Glu Tyr Ser Asp
85 90 95

```
Gly Asn Thr Val Asn Ala Arg Leu Ser Ser Val Ser Pro Gly Gln Gly
            100                 105                 110

Lys Asp Ser Pro Ala Ile Thr Arg Glu Glu Ala Leu Ser Met Ile Lys
        115                 120                 125

Asp Cys Glu Met Ser Ile Asn Ile Lys Cys Ser Glu Glu Glu Lys Asp
    130                 135                 140

Ser Asn Ile Lys Thr His Pro Val Leu Gly Ser Asn Ile Ser His Lys
145                 150                 155                 160

Lys Val Ser Tyr Glu Asp Ile Ile Gly Ser Thr Ile Val Asp Thr Lys
                165                 170                 175

Cys Val Lys Asn Leu Glu Ile Ser Val Arg Ile Gly Asp Met Cys Lys
            180                 185                 190

Glu Ser Ser Glu Leu Glu Val Lys Asp Gly Phe Lys Tyr Val Asp Gly
        195                 200                 205

Ser Ala Ser Glu Asp Ala Ala Asp Asp Thr Ser Leu Ile Asn Ser Ala
    210                 215                 220

Lys Leu Ile Ala Cys Val
225                 230
```

( 2 ) INFORMATION FOR SEQ ID NO:3:

( i ) SEQUENCE CHARACTERISTICS:
( A ) LENGTH: 777 base pairs
( B ) TYPE: nucleic acid
( C ) STRANDEDNESS: single
( D ) TOPOLOGY: linear ( i i ) MOLECULE TYPE: cDNA ( i i i ) HYPOTHETICAL: NO ( i v ) ANTI-SENSE: NO ( v i i ) IMMEDIATE SOURCE:
( B ) CLONE: Vaccinia p35

( i x ) FEATURE:
( A ) NAME/KEY: CDS
( B ) LOCATION: 1..777

( i x ) FEATURE:
( A ) NAME/KEY: mat_peptide
( B ) LOCATION: 52..774

( i x ) FEATURE:
( A ) NAME/KEY: sig_peptide
( B ) LOCATION: 1..51

( x i ) SEQUENCE DESCRIPTION: SEQ ID NO:3:

```
ATG AAA CAA TAT ATC GTC CTG GCA TGC ATG TGC CTG GCG GCA GCT GCT      48
Met Lys Gln Tyr Ile Val Leu Ala Cys Met Cys Leu Ala Ala Ala Ala
-17     -15                 -10                  -5

ATG CCT GCC AGT CTT CAG CAA TCA TCC TCA TCC TCC TCC TCG TGT ACG      96
Met Pro Ala Ser Leu Gln Gln Ser Ser Ser Ser Ser Ser Ser Cys Thr
      1                   5                  10                  15

GAA GAA GAA AAC AAA CAT CAT ATG GGA ATC GAT GTT ATT ATC AAA GTC     144
Glu Glu Glu Asn Lys His His Met Gly Ile Asp Val Ile Ile Lys Val
                 20                  25                  30

ACA AAG CAA GAC CAA ACA CCG ACC AAT GAT AAG ATT TGC CAA TCC GTA     192
Thr Lys Gln Asp Gln Thr Pro Thr Asn Asp Lys Ile Cys Gln Ser Val
             35                  40                  45

ACG GAA ATT ACA GAG TCC GAG TCA GAT CCA GAT CCC GAG GTG GAA TCA     240
Thr Glu Ile Thr Glu Ser Glu Ser Asp Pro Asp Pro Glu Val Glu Ser
         50                  55                  60
```

-continued

```
GAA GAT GAT TCC ACA TCA GTC GAG GAT GTA GAT CCT CCT ACC ACT TAT      288
Glu Asp Asp Ser Thr Ser Val Glu Asp Val Asp Pro Pro Thr Thr Tyr
     65                 70                  75

TAC TCC ATC ATC GGT GGA GGT CTG AGA ATG AAC TTT GGA TTC ACC AAA      336
Tyr Ser Ile Ile Gly Gly Gly Leu Arg Met Asn Phe Gly Phe Thr Lys
 80                  85                  90                  95

TGT CCT CAG ATT AAA TCC ATC TCA GAA TCC GCT GAT GGA AAC ACA GTG      384
Cys Pro Gln Ile Lys Ser Ile Ser Glu Ser Ala Asp Gly Asn Thr Val
                100                 105                 110

AAT GCT AGA TTG TCC AGC GTG TCC CCA GGA CAA GGT AAG GAC TCT CCC      432
Asn Ala Arg Leu Ser Ser Val Ser Pro Gly Gln Gly Lys Asp Ser Pro
            115                 120                 125

GCG ATC ACT CGT GAA GAA GCT CTT GCT ATG ATC AAA GAC TGT GAG GTG      480
Ala Ile Thr Arg Glu Glu Ala Leu Ala Met Ile Lys Asp Cys Glu Val
        130                 135                 140

TCT ATC GAC ATC AGA TGT AGC GAA GAA GAG AAA GAC AGC GAC ATC AAG      528
Ser Ile Asp Ile Arg Cys Ser Glu Glu Glu Lys Asp Ser Asp Ile Lys
    145                 150                 155

ACC CAT CCA GTA CTC GGG TCT AAC ATC TCT CAT AAG AAA GTG AGT TAC      576
Thr His Pro Val Leu Gly Ser Asn Ile Ser His Lys Lys Val Ser Tyr
160                 165                 170                 175

GAA GAT ATC ATC GGT TCA ACG ATC GTC GAT ACA AAA TGT GTC AAG AAT      624
Glu Asp Ile Ile Gly Ser Thr Ile Val Asp Thr Lys Cys Val Lys Asn
                180                 185                 190

CTA GAG TTT AGC GTT CGT ATC GGA GAC ATG TGC AAG GAA TCA TCT GAA      672
Leu Glu Phe Ser Val Arg Ile Gly Asp Met Cys Lys Glu Ser Ser Glu
            195                 200                 205

CTT GAG GTC AAG GAT GGA TTC AAG TAT GTC GAC GGA TCG GCA TCT GAA      720
Leu Glu Val Lys Asp Gly Phe Lys Tyr Val Asp Gly Ser Ala Ser Glu
        210                 215                 220

GGT GCA ACC GAT GAT ACT TCA CTC ATC GAT TCA ACA AAA CTC AAA GCG      768
Gly Ala Thr Asp Asp Thr Ser Leu Ile Asp Ser Thr Lys Leu Lys Ala
    225                 230                 235

TGT GTC TGA                                                          777
Cys Val  *
240
```

( 2 ) INFORMATION FOR SEQ ID NO:4:

( i ) SEQUENCE CHARACTERISTICS:
( A ) LENGTH: 258 amino acids
( B ) TYPE: amino acid
( D ) TOPOLOGY: linear ( i i ) MOLECULE TYPE: protein ( x i ) SEQUENCE DESCRIPTION: SEQ ID NO:4:

```
Met Lys Gln Tyr Ile Val Leu Ala Cys Met Cys Leu Ala Ala Ala Ala
-17     -15                 -10                  -5

Met Pro Ala Ser Leu Gln Gln Ser Ser Ser Ser Ser Ser Ser Cys Thr
      1               5                  10                  15

Glu Glu Glu Asn Lys His His Met Gly Ile Asp Val Ile Ile Lys Val
                 20                  25                  30

Thr Lys Gln Asp Gln Thr Pro Thr Asn Asp Lys Ile Cys Gln Ser Val
             35                  40                  45

Thr Glu Ile Thr Glu Ser Glu Ser Asp Pro Asp Pro Glu Val Glu Ser
         50                  55                  60

Glu Asp Asp Ser Thr Ser Val Glu Asp Val Asp Pro Pro Thr Thr Tyr
     65                  70                  75

Tyr Ser Ile Ile Gly Gly Gly Leu Arg Met Asn Phe Gly Phe Thr Lys
 80                  85                  90                  95
```

-continued

| | | | | | | | | | | | | | | | |
|---|---|---|---|---|---|---|---|---|---|---|---|---|---|---|---|
| Cys | Pro | Gln | Ile | Lys<br>100 | Ser | Ile | Ser | Glu | Ser<br>105 | Ala | Asp | Gly | Asn | Thr<br>110 | Val |
| Asn | Ala | Arg | Leu<br>115 | Ser | Ser | Val | Ser | Pro<br>120 | Gly | Gln | Gly | Lys | Asp<br>125 | Ser | Pro |
| Ala | Ile | Thr<br>130 | Arg | Glu | Glu | Ala | Leu<br>135 | Ala | Met | Ile | Lys | Asp<br>140 | Cys | Glu | Val |
| Ser | Ile<br>145 | Asp | Ile | Arg | Cys | Ser<br>150 | Glu | Glu | Glu | Lys | Asp<br>155 | Ser | Asp | Ile | Lys |
| Thr<br>160 | His | Pro | Val | Leu | Gly<br>165 | Ser | Asn | Ile | Ser | His<br>170 | Lys | Lys | Val | Ser | Tyr<br>175 |
| Glu | Asp | Ile | Ile | Gly<br>180 | Ser | Thr | Ile | Val | Asp<br>185 | Thr | Lys | Cys | Val | Lys<br>190 | Asn |
| Leu | Glu | Phe | Ser<br>195 | Val | Arg | Ile | Gly | Asp<br>200 | Met | Cys | Lys | Glu | Ser<br>205 | Ser | Glu |
| Leu | Glu | Val<br>210 | Lys | Asp | Gly | Phe | Lys<br>215 | Tyr | Val | Asp | Gly | Ser<br>220 | Ala | Ser | Glu |
| Gly | Ala<br>225 | Thr | Asp | Asp | Thr | Ser<br>230 | Leu | Ile | Asp | Ser | Thr<br>235 | Lys | Leu | Lys | Ala |
| Cys<br>240 | Val | | | | | | | | | | | | | | |

( 2 ) INFORMATION FOR SEQ ID NO:5:

( i ) SEQUENCE CHARACTERISTICS:
( A ) LENGTH: 762 base pairs
( B ) TYPE: nucleic acid
( C ) STRANDEDNESS: single
( D ) TOPOLOGY: linear ( i i ) MOLECULE TYPE: cDNA to mRNA ( i i i ) HYPOTHETICAL: NO ( i v ) ANTI-SENSE: NO ( v i i ) IMMEDIATE SOURCE:
( B ) CLONE: Variola p35

( i x ) FEATURE:
( A ) NAME/KEY: CDS
( B ) LOCATION: 1..762

( i x ) FEATURE:
( A ) NAME/KEY: mat_peptide
( B ) LOCATION: 49..759

( i x ) FEATURE:
( A ) NAME/KEY: sig_peptide
( B ) LOCATION: 1..48

( x i ) SEQUENCE DESCRIPTION: SEQ ID NO:5:

| | | | | | | | | | | | | | | | | |
|---|---|---|---|---|---|---|---|---|---|---|---|---|---|---|---|---|
| ATG<br>Met<br>-16 | AAA<br>Lys<br>-15 | CAA<br>Gln | TAT<br>Tyr | ATC<br>Ile | GTC<br>Val | CTG<br>Leu<br>-10 | GCA<br>Ala | TGC<br>Cys | ATG<br>Met | TGC<br>Cys | CTG<br>Leu<br>-5 | GCG<br>Ala | GCA<br>Ala | GCT<br>Ala | GCT<br>Ala | 48 |
| ATG<br>Met<br>1 | CCT<br>Pro | GCC<br>Ala | AGT<br>Ser | CTT<br>Leu<br>5 | CAG<br>Gln | CAA<br>Gln | TCC<br>Ser | TCA<br>Ser | TCC<br>Ser<br>10 | TCG<br>Ser | TGT<br>Cys | ACT<br>Thr | GAA<br>Glu | GAA<br>Glu<br>15 | GAA<br>Glu | 96 |
| AAC<br>Asn | AAA<br>Lys | CAT<br>His | TAT<br>Tyr<br>20 | ATG<br>Met | GGA<br>Gly | ATC<br>Ile | GAT<br>Asp | GTT<br>Val<br>25 | ATT<br>Ile | ATC<br>Ile | AAA<br>Lys | GTC<br>Val | ACA<br>Thr<br>30 | AAG<br>Lys | CAA<br>Gln | 144 |
| GAC<br>Asp | CAA<br>Gln | ACA<br>Thr<br>35 | CCG<br>Pro | ACC<br>Thr | AAT<br>Asn | GAT<br>Asp | AAG<br>Lys<br>40 | ATT<br>Ile | TGC<br>Cys | CAA<br>Gln | TCC<br>Ser | GTA<br>Val<br>45 | ACG<br>Thr | GAA<br>Glu | ATT<br>Ile | 192 |
| ACA | GAG | TCC | GAG | TCA | GAT | CCC | GAG | GTG | GAA | TCA | GAA | GAT | GAT | TCC | ACA | 240 |

-continued

Thr Glu Ser Glu Ser Asp Pro Glu Val Glu Ser Glu Asp Asp Ser Thr
50 55 60

TCA GTC GAG GAT GTA GAT CCT CCT ACC ACT TAT TAC TCC ATT ATT GGC 288
Ser Val Glu Asp Val Asp Pro Pro Thr Thr Tyr Tyr Ser Ile Ile Gly
65 70 75 80

GGA GGT CTG AGA ATG AAC TTT GGA TTC ACC AAA TGT CCT CAG ATT AAA 336
Gly Gly Leu Arg Met Asn Phe Gly Phe Thr Lys Cys Pro Gln Ile Lys
85 90 95

TCC ATC TCA GAA TCC GCT AAT GGA AAC GCA GTG AAT GCT AGA TTG TCC 384
Ser Ile Ser Glu Ser Ala Asn Gly Asn Ala Val Asn Ala Arg Leu Ser
100 105 110

AGC GTG CCC CTA GGA CAA GGT AAG GAC TCT CCC GCT ATC ACT CGT GCA 432
Ser Val Pro Leu Gly Gln Gly Lys Asp Ser Pro Ala Ile Thr Arg Ala
115 120 125

GAA GCT CTG GCT ATG ATC AAA GAC TGT GAG CTG TCT ATC GAC ATT AGA 480
Glu Ala Leu Ala Met Ile Lys Asp Cys Glu Leu Ser Ile Asp Ile Arg
130 135 140

TGT AGC GAA GAA GAG AAA GAC AGC GAC ATC CAG ACC CAT CCA GTA CTC 528
Cys Ser Glu Glu Glu Lys Asp Ser Asp Ile Gln Thr His Pro Val Leu
145 150 155 160

GAG TCT AAC ATC TCT CAT AAG AAA GTG AGT TAC GAA GAT ATC ATC GGT 576
Glu Ser Asn Ile Ser His Lys Lys Val Ser Tyr Glu Asp Ile Ile Gly
165 170 175

TCA ACG ATC GTT GAT ACA AAA TGC GTC AAG AAT CTA GAG TTT AGT GTT 624
Ser Thr Ile Val Asp Thr Lys Cys Val Lys Asn Leu Glu Phe Ser Val
180 185 190

CGT ATC GGA GAC ATG TGC AAG GAA TCG TCT GAT CTT GAG GTC AAG GAT 672
Arg Ile Gly Asp Met Cys Lys Glu Ser Ser Asp Leu Glu Val Lys Asp
195 200 205

GGA TTT AAG TAT GTC GAC GGA TCG GTA TCT GAA GGT GTA ACC GAT GAT 720
Gly Phe Lys Tyr Val Asp Gly Ser Val Ser Glu Gly Val Thr Asp Asp
210 215 220

ACT TCA CTC ATC GAT TCA ACA AAA CTC AAA TCG TGT GTC TGA 762
Thr Ser Leu Ile Asp Ser Thr Lys Leu Lys Ser Cys Val *
225 230 235

( 2 ) INFORMATION FOR SEQ ID NO:6:

( i ) SEQUENCE CHARACTERISTICS:
( A ) LENGTH: 253 amino acids
( B ) TYPE: amino acid
( D ) TOPOLOGY: linear ( i i ) MOLECULE TYPE: protein ( x i ) SEQUENCE DESCRIPTION: SEQ ID NO:6:

Met Lys Gln Tyr Ile Val Leu Ala Cys Met Cys Leu Ala Ala Ala Ala
-16 -15 -10 -5

Met Pro Ala Ser Leu Gln Gln Ser Ser Ser Ser Cys Thr Glu Glu Glu
1 5 10 15

Asn Lys His Tyr Met Gly Ile Asp Val Ile Ile Lys Val Thr Lys Gln
20 25 30

Asp Gln Thr Pro Thr Asn Asp Lys Ile Cys Gln Ser Val Thr Glu Ile
35 40 45

Thr Glu Ser Glu Ser Asp Pro Glu Val Glu Ser Glu Asp Asp Ser Thr
50 55 60

Ser Val Glu Asp Val Asp Pro Pro Thr Thr Tyr Tyr Ser Ile Ile Gly
65 70 75 80

Gly Gly Leu Arg Met Asn Phe Gly Phe Thr Lys Cys Pro Gln Ile Lys
85 90 95

-continued

Ser Ile Ser Glu Ser Ala Asn Gly Asn Ala Val Asn Ala Arg Leu Ser
100 105 110

Ser Val Pro Leu Gly Gln Gly Lys Asp Ser Pro Ala Ile Thr Arg Ala
115 120 125

Glu Ala Leu Ala Met Ile Lys Asp Cys Glu Leu Ser Ile Asp Ile Arg
130 135 140

Cys Ser Glu Glu Glu Lys Asp Ser Asp Ile Gln Thr His Pro Val Leu
145 150 155 160

Glu Ser Asn Ile Ser His Lys Lys Val Ser Tyr Glu Asp Ile Ile Gly
165 170 175

Ser Thr Ile Val Asp Thr Lys Cys Val Lys Asn Leu Glu Phe Ser Val
180 185 190

Arg Ile Gly Asp Met Cys Lys Glu Ser Ser Asp Leu Glu Val Lys Asp
195 200 205

Gly Phe Lys Tyr Val Asp Gly Ser Val Ser Glu Gly Val Thr Asp Asp
210 215 220

Thr Ser Leu Ile Asp Ser Thr Lys Leu Lys Ser Cys Val
225 230 235

( 2 ) INFORMATION FOR SEQ ID NO:7:

( i ) SEQUENCE CHARACTERISTICS:
( A ) LENGTH: 8 amino acids
( B ) TYPE: amino acid
( C ) STRANDEDNESS: single
( D ) TOPOLOGY: linear ( i i ) MOLECULE TYPE: peptide ( i i i ) HYPOTHETICAL: NO ( i v ) ANTI-SENSE: NO ( v i i ) IMMEDIATE SOURCE:
( B ) CLONE: FLAG peptide ( x i ) SEQUENCE DESCRIPTION: SEQ ID NO:7:

Asp Tyr Lys Asp Asp Asp Asp Lys
1 5